United States Patent [19]
Dent et al.

[11] Patent Number: 5,988,452
[45] Date of Patent: Nov. 23, 1999

[54] DISPENSING MECHANISM AND METHOD FOR DELIVERING MEASURED DOSES WITH SLOTTED PLUNGER

[75] Inventors: Hugh Dent, Corsley, United Kingdom; Mark L. Anderson, Spring Valley, Wis.

[73] Assignee: Mark Anderson, Spring Valley, Wis.

[21] Appl. No.: 09/093,737

[22] Filed: Jun. 8, 1998

Related U.S. Application Data

[63] Continuation-in-part of application No. 09/007,089, Jan. 14, 1998, abandoned.

[30] Foreign Application Priority Data

Jan. 14, 1997 [GB] United Kingdom .................... 9700609

[51] Int. Cl.$^6$ .................................................. B65D 88/54
[52] U.S. Cl. .............................. 222/309; 222/43; 604/208
[58] Field of Search .............................. 222/309, 43, 631, 222/634, 287; 604/210, 211, 38, 154, 155, 208

[56] References Cited

U.S. PATENT DOCUMENTS

| | | |
|---|---|---|
| 2,605,763 | 8/1952 | Smoot ........................................ 604/70 |
| 2,736,315 | 2/1956 | Feneey ...................................... 604/211 |
| 3,831,602 | 8/1974 | Broadwin . | 
| 4,564,360 | 1/1986 | Young et al. . |
| 4,678,107 | 7/1987 | Ennis, III . |
| 4,852,772 | 8/1989 | Ennis, III . |
| 4,923,096 | 5/1990 | Ennis, III . |
| 4,981,472 | 1/1991 | Ennis, III et al. . |
| 5,344,409 | 9/1994 | Ennis, III et al. . |

FOREIGN PATENT DOCUMENTS

| | | |
|---|---|---|
| 1 412 312 | 11/1975 | United Kingdom . |
| 2 196 534 | 5/1988 | United Kingdom . |

*Primary Examiner*—Henry J. Recla
*Assistant Examiner*—Peter DeVore
*Attorney, Agent, or Firm*—Skinner and Associates

[57] ABSTRACT

A dispensing mechanism for an applicator having a cylinder and a plunger. The plunger has a piston head slidable in liquid-tight manner within the cylinder. The plunger performs an expansion stroke to draw fluid into the cylinder and performs a compression stroke to dispense fluid from the cylinder. The dispensing mechanism includes a stop member attached to the cylinder of the applicator. The stop member has an engagement part extending toward the plunger. The plunger has at least one abutment formed on its surface for contacting the engagement part and limiting the motion of the plunger. Each abutment preferably comprises an end surface of a longitudinal groove formed in the surface. The engagement part tracks within the longitudinal groove and preferably limits the expansion stroke when the engagement part contacts the end surface. Each longitudinal groove is of a different length corresponding to a desired dose volume in the cylinder. The engagement part can track to a desired longitudinal groove through the circumferencial groove.

24 Claims, 4 Drawing Sheets

DISPENSING MECHANISM AND METHOD FOR DELIVERING MEASURED DOSES WITH SLOTTED PLUNGER

CROSS-REFERENCE TO RELATED APPLICATIONS, IF ANY

This application is a continuation-in-part under 37 CFR 1.53(b)(1) of application Ser. No. 09/007,089, filed Jan. 14, 1998, abandoned, which claimed the benefit under 35 U.S.C. §119(a) of British Patent Application No. 9700609.2 entitled "Drencher with Slotted Plunger" filed Jan. 14, 1997 in the name of Rembrook Developments Limited.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention.

The invention relates to apparatus and methods for dispensing measured doses and particularly, but not exclusively, to apparatus and methods for dispensing measured liquid doses from applicators that generally comprise a plunger with a piston head sealingly fit within a cylinder. The invention is particularly applicable to applicators for veterinary purposes such as dosing animals with liquid, paste or gel medicaments. However, it will be appreciated from the following description that the invention is not limited to such applications and may be used for many other purposes where it is necessary to dispense repeated measured doses of a liquid.

2. Background.

The state of the art includes various applicator devices and methods for dispensing measured liquid doses. State of the art applicators include drenchers, trigger pumps, and syringes. These applicators or delivery systems typically comprise a cylinder and an elongate plunger. The plunger has a piston head which is slidable in a liquid-tight manner within the cylinder to discharge fluid from the cylinder through an outlet and draw fluid in through an inlet. The outlet and inlet may be the same orifice as is the case in a basic syringe. It is desirable to be able to preset the volume of liquid which is discharged from the cylinder in each compression stroke of the plunger. The preset volume of discharged liquid may be determined either by the volumetric dimensions of the cylinder as it relates to a complete plunger stroke or by a predetermined limited motion of the plunger within the cylinder. For example, there may be provided an adjustable stop arrangement for limiting the motion of the plunger either in the compression stroke direction or in the expansion stroke direction. It is preferred to limit the movement of the plunger in the expansion stroke direction to ensure that the cylinder is completely discharged after each compression stroke, regardless of the volume of liquid being discharged.

Drenchers and trigger pumps administer fixed doses of fluid either from an attached container or from an external bulk supply. An example of a trigger pump is disclosed in U.S. patent application No. 08/870,918 entitled Fluid Dispenser Apparatus filed on Jun. 6, 1997 in the name of Mark Anderson, and is hereby incorporated by reference. These devices typically have a squeezable trigger or handle used to expel the fluid from the cylinder. A fixed dose amount, predetermined by the volume of the cylinder, is accurately dispensed by moving the trigger or handle through its full range of motion, which causes the plunger to undergo complete compression and expansion stroke. Although an estimated partial dose can be delivered by partially moving the trigger or handle through its range of motion, an accurate administration of a different sized dose generally requires another applicator having a cylinder sized to contain the desired dose volume.

The syringe type devices provide a generally simpler method of dispensing doses. Syringe type devices are generally shown in the following art: Ennis, III (U.S. Pat. No. 4,923,096) which describes a dripless automatic syringe for dispensing fluids; Ennis, III (U.S. Pat. No. 5,344,409) which describes a syringe latch; Ennis, III (U.S. Pat. No. 4,852,772) which describes a dispenser for viscous fluids; Ennis, III (U.S. Pat. No. 4,678,107) which describes a dripless dispenser for liquids and viscous fluids; and Ennis, III (U.S. Pat. No. 4,981,472) which describes a cannula assembly for a syringe. Generally, a desired dose is drawn into the syringe by carefully monitoring graduated markings on the cylinder. Alternatively, a syringe latch can be attached and reattached to the plunger to repeatably and accurately meter incremental doses of fluid by limiting the compression stroke of the plunger.

The known art is believed to have significant limitations and shortcomings. Specifically, they are unable to provide an economical, efficient, and effective means for dispensing a range of accurate doses from a variety of delivery systems, including the applicators described above. Applicant's invention provides an mechanism and method for dispensing measured doses which is believed to constitute an improvement over the known art.

BRIEF SUMMARY OF THE INVENTION

The present invention provides a mechanism and method for dispensing measured doses from a delivery system or applicator, such as a drencher, trigger pump or syringe, that generally comprises a plunger having a piston head slidable in a liquid-tight manner within a cylinder. The dispensing mechanism is incorporated with the applicator. The dispensing mechanism of the present invention includes a stop member attached to the cylinder either directly or indirectly. The stop member has a projection that cooperates with or engages one of a plurality of abutments formed on the surface of plunger. The abutments are formed by the end surface of grooves aligned with the longitudinal axis of the plunger. The grooves preferably have various lengths so that the abutments are staggered at desired positions along the length of the plunger. The abutments contact the projection of the stop member to limit the movement of the plunger. Each of the staggered abutments formed by the longitudinal grooves are preferably circumferencially spaced at different axial positions on the plunger. The stop device is aligned with a desired longitudinal groove to limit the motion of the plunger within the cylinder to correspond to the desired dose volume.

In addition to relative longitudinal motion, the stop device and plunger preferably are capable of relative rotational movement to render the stop device engageable by a particular abutment. Preferably the plunger is non-rotatable relative to the cylinder and the stop member is rotatable relative to the cylinder and plunger, although it may be desirable for the plunger to be rotatable and for the stop member to be non-rotatable with respect to the cylinder for a particular applicator.

The plunger may be formed with a circumferencial slot or groove which intersects the longitudinal slots or grooves, allowing the stop member to rotate around the plunger to a desired axial position when the projection of the stop member is located in the circumferencial slot or groove. A preferred embodiment positions the circumferencial slot or groove on the plunger so that the projection of the stop member enters the circumferencial groove when the plunger has completed a compression stroke and has expelled all of the fluid in the cylinder. An alternative preferred embodiment for metering the dispensed volume positions the circumferencial slot or groove on the plunger so that the projection of the stop member enters the circumferencial groove when the plunger has completed an expansion stroke.

The stop member may be formed with a cooperating pointer and scale whereby the scale indicates the volume of liquid to be dispensed from the cylinder when the projection of the stop member is in a particular groove. The stop member may comprise a generally annular member encircling the plunger. The projection projects inwardly from the inner periphery of the annular member to engage the abutments.

The applicator may further include inlet means to draw fluid into the cylinder and outlet means to expel fluid from the cylinder. The inlet means may be controlled by a nonreturn valve and another non-return valve may be provided to control the outlet means of the cylinder. The inlet means may comprise an inlet passage passing longitudinally through said plunger or the outlet means may comprise an outlet passage passing longitudinally through said plunger. The applicator may further include spring means for biasing the plunger in the cylinder. The dispensing mechanism of the present invention can be incorporated and used in a variety of applicators, including drenchers, trigger pumps, and syringes.

Significant features of the invention include the versatility of use in a variety of applicators, the limitation of the expansion stroke to draw in a desired dose volume of fluid into the cylinder, the number of accurate dose volumes that can be distributed from a single applicator, and the ease of adjusting the desired dose volume.

The features, benefits and objects of this invention will become clear to those skilled in the art by reference to the following description, claims and drawings.

DETAILED DESCRIPTION

Referring to FIGS. 1–5, an example of the preferred embodiment of the measured dose dispensing mechanism, hereinafter dispensing mechanism, of the present invention is illustrated and generally indicated by the reference numeral 10. The dispensing mechanism 10 is described below first in terms of its major structural elements and then in terms of its secondary structural and/or functional elements which cooperate to dispense measured liquid doses out of a variety of applicators or delivery systems.

Figure 1:
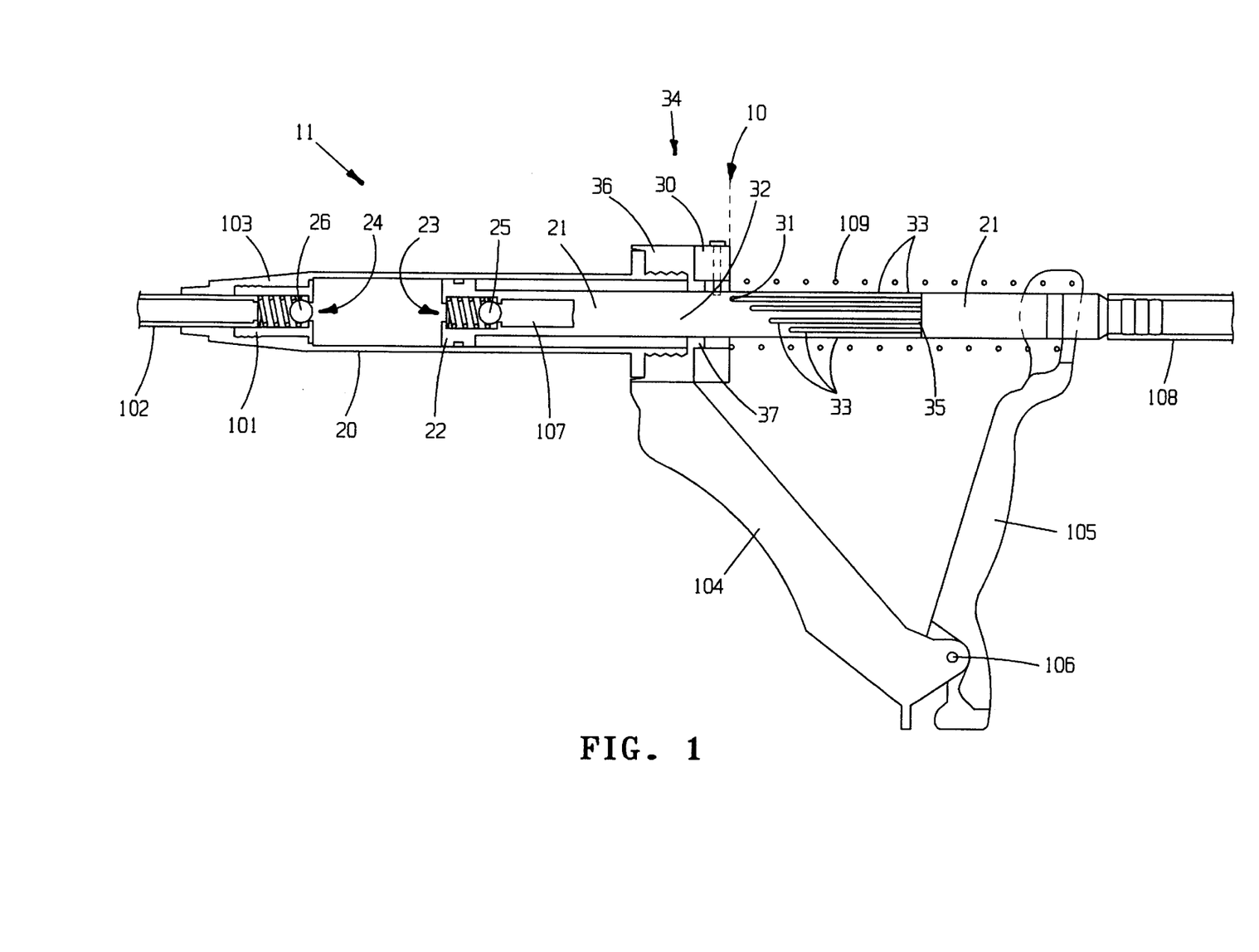
FIG. 1 is a cross-sectional view of a drencher incorporating the dispensing mechanism of the present invention.
Figures 2, 4:
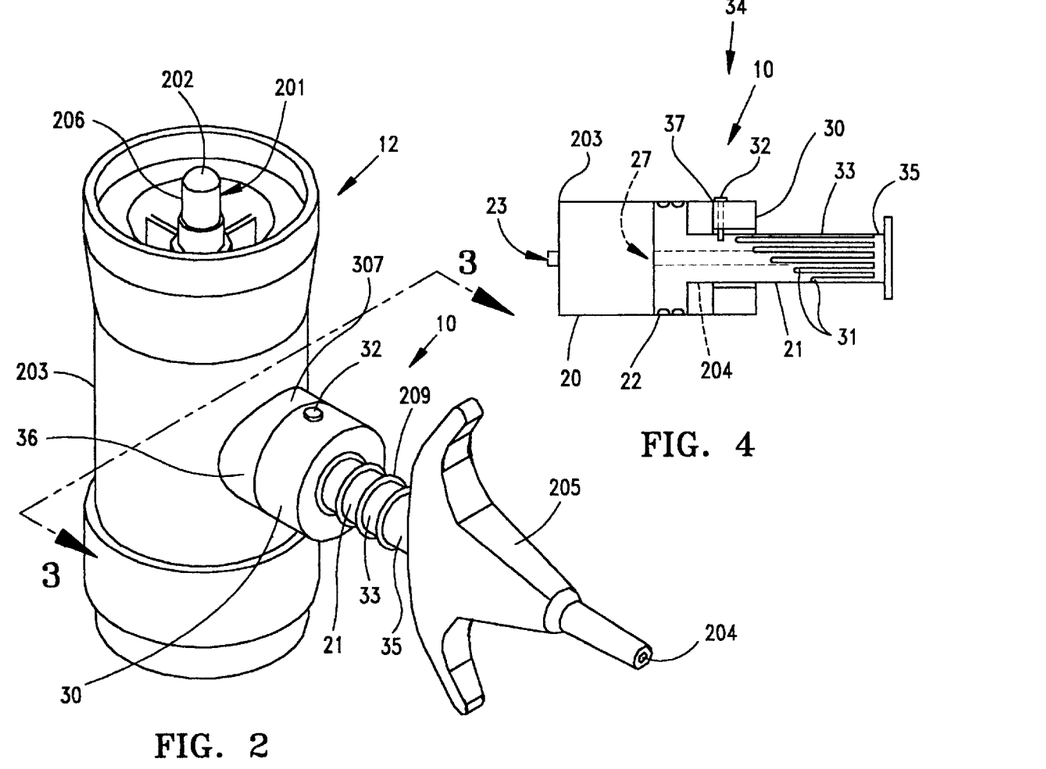
FIG. 2 is a perspective view of a trigger pump incorporating the dispensing mechanism of the present invention.
FIG. 4 is a detailed cross-sectional view of the dispensing mechanism of FIG. 2.
Figure 3:
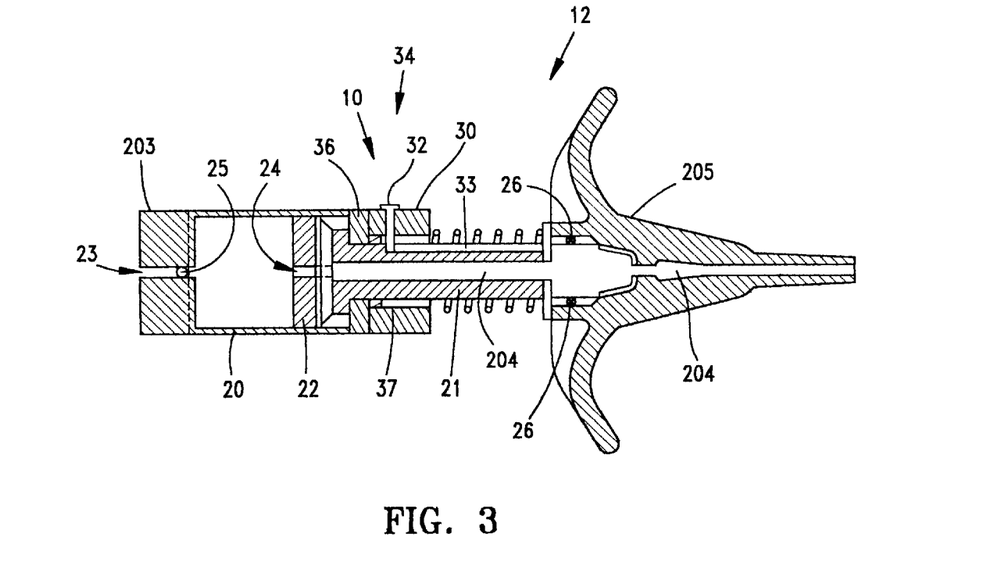
FIG. 3 is an illustrative cross-sectional view taken along line 3—3 of FIG. 2.
Figure 5:
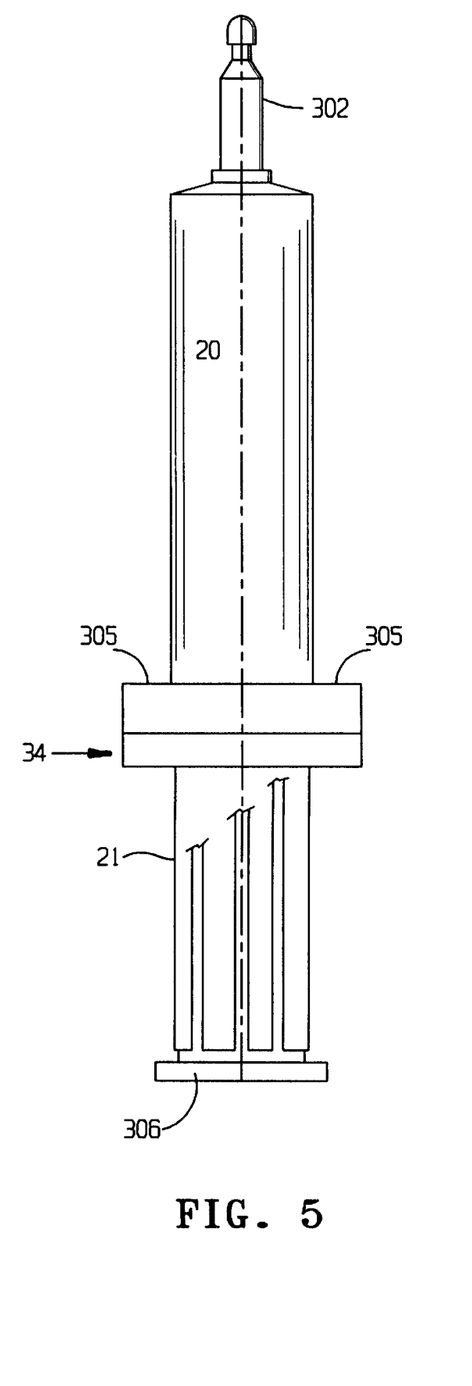
FIG. 5 is a side view of a syringe incorporating the dispensing mechanism of the present invention.
Figure 6:
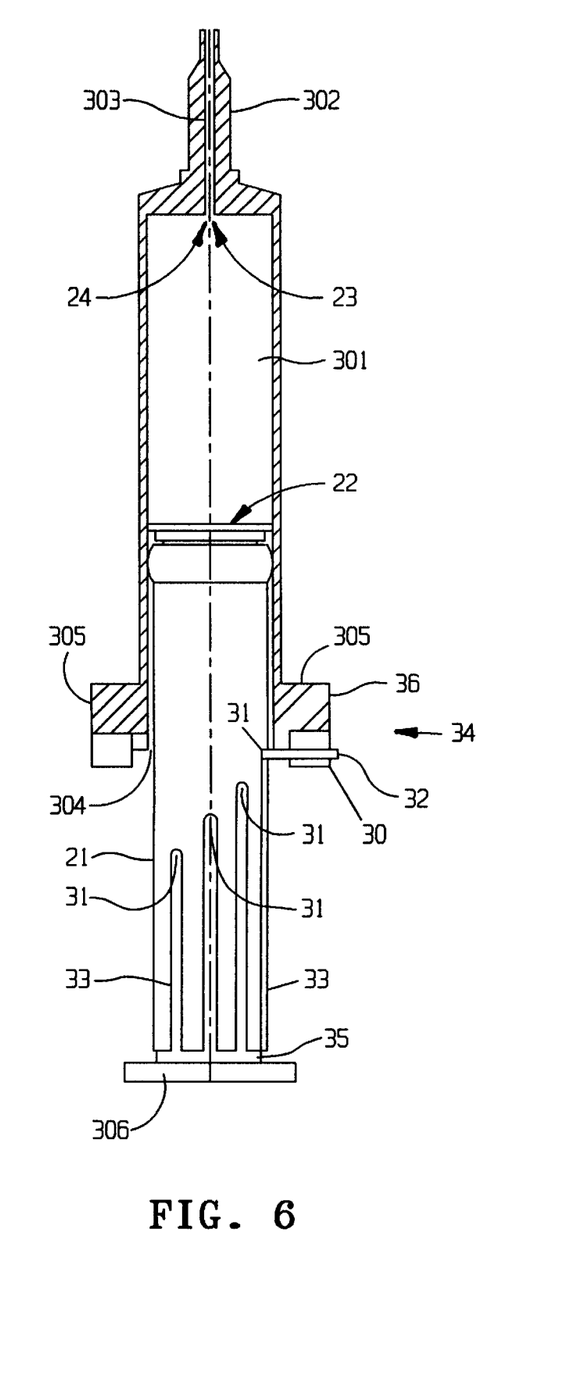
FIG. 6 is a side view, partially in cross section, of the syringe of FIG. 5.

FIG. 1 shows the dispensing mechanism 10 incorporated within drencher applicator 11, FIGS. 2–4 show the dispensing mechanism 10 incorporated within a trigger pump applicator 12, and FIGS. 5–6 show the dispensing mechanism 10 incorporated within a syringe applicator 13. Referring to the figures, all of the applicators 11, 12, and 13 generally have a cylinder 20 within which a plunger 21 reciprocates in a compression and an expansion stroke. The plunger 21 has a piston part 22 which is in liquid-tight or sealingly-fit sliding engagement with the interior surface of the cylinder 20. The applicators 11, 12, and 13 further all have an inlet 23 for receiving or drawing fluid into the cylinder 20 during an expansion stroke of the plunger 21, and an outlet 24 for dispensing or expelling fluid out of the cylinder 20 during a compression stroke of the plunger 21. The inlet 23 and outlet 24 are different orifices for the drencher 11 and the trigger pump 12 applicators, and are the same orifice for the syringe 13 applicator. If the inlet 23 and outlet 24 are comprised of different orifices, an intake one-way valve 25 is positioned in the inlet 23 and an outtake one-way valve 26 is positioned in the outlet 24. Therefore, assuming that the cylinder 20 does not contain fluid and the plunger 21 is at point 34, during the expansion stroke the intake one-way valve 25 allows fluid to enter the cylinder 20 through the inlet 23 while the outtake one-way valve 26 prevents a reverse flow of fluid through the outlet 24. During the compression stroke the outtake one-way valve 26 allows fluid to be expelled out of the outlet 24 while the intake one-way valve 25 prevents a reverse flow of fluid through the inlet 23.

The dispensing mechanism 10 of the present invention is designed to limit the motion of the plunger 21 within the cylinder 20. A stop member 30 is attached to an applicator in a predetermined position with respect to the cylinder 20. The plunger 21 is formed with a plurality of abutments 31 spaced axially around the plunger 21. A projection 32 extending from the stop member 30 relates or contacts with these abutments 31. The abutments 31 are preferably formed from predetermined arrangement of a plurality of grooves 33 formed in the surface of the plunger 21. Preferably, the grooves 33 extend longitudinally along the plunger 21 and are axially spaced around the circumference of the plunger 21. Furthermore, it is preferable that a first end of the grooves 33 are circumferencially aligned along the plunger 21 at a point 34 corresponding to the completion of a compression stroke. The respective end walls at the second end of each of the grooves 33 form the abutments 31. A circumferencial groove 35 preferably intersects each of the longitudinal grooves 33 at a point 34 so that the projection 32 extends into the circumferencial groove 35 when the plunger 21 has completed a compression stroke. Each of the differently-sized longitudinal grooves 33 extend away from the circumferencial groove 35. The projection 32 fits within the grooves 33 and 35, tracks within the longitudinal grooves 33 during the compression and expansion strokes, and tracks from one longitudinal groove 33 to another through the circumferencial groove 35.

During an expansion stroke, the plunger 21 will move until the projection 32 contacts the end wall or abutment 31 for that groove 33. Therefore, the length of a longitudinal groove 33 determines the movement of the plunger 21, and thus corresponds to a predetermined volume of fluid that is drawn into the cylinder 20 during an expansion stroke. During the compression stroke, the plunger 21 expels the predetermined volume of fluid from the cylinder 20. After the compression stroke, the projection 32 is in alignment with the circumferencial groove 35, allowing the plunger 21 and projection 32 to be rotated with respect to each other until the projection 32 aligns with the longitudinal groove 33 that corresponds to a new desired dose volume. Alternatively, rather than using a circumferencial groove 35, the projection 32 could be retracted out of a longitudinal groove 33, realigned with another longitudinal groove 33, and reinserted. Another alternative is to have a plurality of retractable projections pre-aligned with the longitudinal grooves 33, wherein a desired dose volume is selected by inserting a projection into the desired groove 33.

The cylinder 20 preferably has an annular cap 36 including an annular boss or ledge 37 having an aperture sized to permit the plunger 21 to slidingly fit within the cap 36. Furthermore, the stop member 30 is preferably annular and is sized to fit over the ledge 37. The stop member 30 and its projection 32 are preferably rotatable on the ledge 37. The stop member 30 may be held in place using a helical spring as shown in FIGS. 1–3, or alternatively the stop member 30 may be rotatably coupled to the cap 36. If the stop member 30 is affixed to the cap 36, the plunger 21 is preferably rotatable. A pointer 38 and a scale 39 correlating to the dose volume for an aligned groove could be provided on the cap 36 and stop member 30, or alternatively on the plunger 21 and stop member 30.

FIG. 1 illustrates a drencher applicator 11 incorporating the dispensing mechanism 10 of the present invention. The cylinder 20, which is preferably formed of transparent plastic material, is formed at one end with an externally threaded hollow boss 101 within which is tightly received a discharge tube 102. An internally threaded retaining element 103 is screwed onto the boss 101 to retain the tube 102 in the boss 101. An outtake one-way valve 26 is located in the boss 101 to prevent fluid passing into the cylinder 20 through the discharge tube 102.

The opposite end of the cylinder 20 is screwed into an annular end cap 36 on which is integrally formed a fixed handle part 104. The plunger 21, which may also be formed from a plastic material, extends through the end cap 36 coaxially with the cylinder 20 and is engaged by the upper part of a movable handle part 105, the lower end of which is pivotally connected to the fixed handle part 104, as indicated at 106. A fluid ingress channel or central passage 107 extends longitudinally within the plunger 21, and located in the end of the plunger 21 adjacent the piston head 22 is an intake one-way valve 25 arranged to prevent the escape of liquid from the cylinder 20 along the passage 107. The free end of the hollow plunger 21 is connected by a flexible tube 108 to a bulk supply of the fluid to be dispensed (not shown).

A helical compression spring 109 encircles the plunger 21 between the two handle parts 104 and 105, and serves to bias the handle parts away from one another, and hence serves to bias the piston head 22 towards the full expansion position where it lies at the right hand end of the cylinder 20.

The general operation of the drencher applicator 11 is as follows. With the part of the cylinder 20 between the piston head 22 and the valve 26 filled with liquid, the operator squeezes the movable handle part 105 towards the fixed handle part 104, against the action of the compression spring 109, causing the piston head 22 to undergo its compression stroke by moving to the left as seen in FIG. 1. While this is occurring, the outtake one-way valve 26 opens under the liquid pressure, and the liquid is discharged through the discharge tube 102. The intake one-way valve 25 prevents liquid being discharged from the cylinder 20 along the passage 107 in the plunger 21.

Once all the liquid in the cylinder has been discharged, the operator releases the pressure on the handle part 105 and the spring 109 returns the piston head 22 and plunger 21 to the limit of its movement in the expansion direction. During this movement the outtake one-way valve 26 closes so that no previously discharged liquid can be drawn back into the cylinder 20. At the same time, the pressure of supply liquid in the dicharge tube 102 and passage 107 opens the intake one-way valve 25 so that a fresh charge of liquid is delivered along the passage 107 into the cylinder 20, ready for the next operation of the applicator 11.

It will be appreciated that the actual volume of liquid drawn into the cylinder 20 will depend on the distance through which the plunger 21 is retracted under the action of the compression spring 109. This distance is controlled by the dispensing mechanism 10.

The dispensing mechanism 10 is incorporated into the drencher applicator 11 as follows. The plunger 21 is formed along its length with a series of shallow longitudinal grooves 33 extending from a circumferential groove 35. The longitudinal grooves 33 are of different lengths and there may, for example, be provided fourteen grooves 33 around the periphery of the plunger 21 varying in length from about 55 mm to 3 mm. The end wall of each groove 33 forms an abutment 31 for limiting the expansion stroke of the plunger 21.

Encircling a hollow boss 37 on the cap member 36 is an annular adjustable stop member 30 which is formed on its inner periphery with a projection 32 which engages within one of the grooves 33. The projection 32 may, as shown, comprise the inner end of a screw threaded element which passes radially through the stop member 30. Furthermore, the projection 32 may be retractable out of the stop member 30.

As the plunger 21 is retracted under the action of the spring 109 the groove 33, in which the projection 32 is engaged can slide past the projection 32 until the abutment 31 of the groove 33 engages the projection 32, whereupon expansion movement of the plunger 21 is halted. The extent of movement of the plunger 21, and hence the volume of liquid drawn into the cylinder 20, therefore depends on the length of the groove 33 with which the projection 32 is in engagement. Accordingly, the discharge volume may be adjusted by engaging the projection 32 with a different selected groove 33 in the plunger 21.

In order to effect such adjustment the movable handle part 105 is squeezed towards the fixed handle part 104 until the piston head 22 engages the outlet end of the cylinder 20. In this position the projection 32 comes into engagement with the circumferential groove 35 in the plunger 21. It is then possible to rotate the stop member 30 about the axis of the plunger 21 until it is lined up with the open end of a desired groove 33. A cooperating pointer and scale (not shown) is provided on the stop member 30 and end cap 36 to indicate the effective volumes of the cylinder 20 which are associated with the various rotational positions of the stop member 30. The stop member 30 is thus simply rotated until the scale indicates the desired volume of the dose to be discharged. Once the stop member 30 has been rotated to the desired position, the movable handle part 105 is released and the plunger 21 is retracted by the spring 109 to an extent determined by the length of the groove 33 which has been selected. Thus, if the projection 32 has been aligned with a very short groove 33 the plunger 21 will only retract for a correspondingly short distance before the projection 32 strikes the abutment 31 of the groove 33, and only a small amount of liquid will be drawn into the cylinder 20 for subsequent discharge. The barrel of the transparent cylinder 20 may also be marked along it length with a scale indicating the volume enclosed between the piston head 22 and the end of the cylinder 20.

The annular stop member 30 and end cap 36 interlock. The pressure of the compression spring 109 retains the stop member 30 against the end cap 36. Accordingly, the described construction may be simple and cheap to manufacture, comprising only comparatively few components. Also the parts of the applicator 11, and particularly the parts comprising the adjustable stop mechanisms, are easily accessible for cleaning, repair or replacement. Furthermore, all of the components of the applicator 11, apart from the compression spring 109, may conveniently be formed from suitable plastic materials, but it will be appreciated that any other suitable materials might also be employed.

FIGS. 2–4 illustrate a trigger pump applicator 12 incorporating the dispensing mechanism 10 of the present invention. The trigger pump applicator 12 generally comprises: (1) a connection member 201 having a fluid ingress channel 202; (2) a body member 203 having a fluid communication channel (not shown), a dose cylinder 20 of a predetermined volume, and a one-way intake valve 25; (3) a plunger 21 having a piston head 22 positioned in the dose cylinder 20, a one-way outtake valve 26, and a fluid egress channel 204; and (4) a trigger member 205 fixedly connected to the plunger 21.

The general operation of the trigger pump applicator 12 is as follows. An unprimed trigger pump applicator 12 contains air in the fluid ingress channel 202, the fluid communication channel, the dose cylinder 20, the fluid egress channel 204 and the trigger member 205. A compression spring 209 is positioned around the plunger 21 and fits between the body member 203 and the trigger member 205. Squeezing the trigger member 205 compresses the plunger 21 and expels the air from the dose cylinder 20. Releasing the trigger member 205 causes the piston member 21 to undergo an expansion stroke which draws fluid into the fluid ingress channel 202, the fluid communication channel, and the dose cylinder 20. The applicator 12 becomes primed after about two cycles when the applicator 12 contains fluid in all of its channels and cylinders. A primed applicator 12 draws the dose or predetermined volume of fluid into the dose cylinder 20 during the expansion stroke of the plunger 21. The fluid is drawn through the fluid ingress channel 202, the communication channel, and the inlet orifice 23. The dose of fluid is expelled from the dose cylinder 20 through the fluid egress channel 204, the one-way outtake valve 26, and the trigger member 205 during a compression stroke. The dose volume is determined by the predetermined dimensions of the dose cylinder 20 and the predetermined displacement volume of the plunger 21. The dose volume may either be fixed or adjustable. The dispensing mechanism 10 of the present invention provides a desirable method for adjusting the dose volume.

In the "Draw Off" embodiment of the trigger pump applicator 12 shown in FIG. 2, the applicator 12 further includes a fluid stem 206 for drawing off or suctioning fluid from a flexible or rigid fluid source container. The fluid stem 206 contains the fluid ingress channel 202, forms part of the connection member 201, and is constructed to receive a flexible tube. The tube connects the fluid source container to the fluid ingress channel 202. Alternatively, a fluid source container can be screwed or otherwise mounted onto the connection member 201 so that the fluid is in direct contact with the fluid ingress channel 202. In one of the alternative embodiments, the connection member 201 pierces the fluid source container when it is mounted onto the connection member 201. These alternative embodiments (not shown) include an air intake system which equalizes the pressure between the inside and outside of the fluid source by replacing the fluid dispensed out of the container with air, thus providing smoother and easier fluid flow. The air intake system also prevents contaminants from being suctioned back into the applicator and into the medicinal supply.

The dispensing mechanism 10 is incorporated into the trigger pump applicator 12 as follows. The body member 203 has an integral extension that forms an annular cap 36, part of which contains the cylinder. A stop member 30 is rotatably mounted on a ledge 37, wherein the stop member 30 rotates with respect to the body member 203 and the plunger 21. The stop member 30 is held in place on the ledge 37 by the spring 209. The plunger 21 is formed with a plurality of longitudinal grooves 33 of various lengths. A circumferencial groove 35 intersects each of the longitudinal grooves 33 near the base of the trigger member 205. The stop member 30 has a projection 32 which extends and fits into the grooves 33. The projection 32 can track from one longitudinal groove 33 to another via the circumferencial groove 35. Thus the dose volume drawn into the cylinder 20 can be adjusted by squeezing the trigger member 205 completely so that the projection 32 enters the circumferencial groove, aligning the projection 32 with a desired groove 33 using a scale 307 formed on the exterior surface of the cap 36 and the stop member 30, and releasing the trigger member 205 until the projection 32 contacts the corresponding abutment 31.

FIGS. 5–6 illustrate a syringe applicator 13 incorporating the dispensing mechanism 10 of the present invention. The syringe applicator 13 generally includes a hollow body or cylinder 20 and a plunger 21. The cylinder has a chamber 301, a cannula 302 with a bore at a first end 303, an open second end 304, and exterior finger flanges 305 disposed adjacent to the open second end 304. The plunger 21 has a piston head 22 with a ring seal disposed in the cylinder 20 for sealing the chamber 301 at a first end of the plunger 21. The plunger 21 further has a thumb engaging flange 306 fixedly connected to the stem at a second end of the plunger 21.

An operator sets a desired volume of material to be expelled from a syringe applicator 13 using the dispensing mechanism 10, which is incorporated into the syringe applicator 13 as follows. A plurality of longitudinal grooves 33 are formed on the surface of the plunger 21. A circumferencial groove 35 intersects each of the longitudinal grooves 33 corresponding to the place on the plunger 21 proximate to the projection 32 when the plunger 21 has undergone a completed compression stroke. The annular cap 36 is formed using thicker finger flanges 305. A stop member 30 is connected to the cap 36. The projection 32 extends inwardly from the stop member 30 and limits the expansion stroke of the plunger 21, depending on the particular groove 33 in which the projection has entered. The stop member 30 is rotatable with respect to the plunger 21. If the plunger 21 does not rotate, then the stop member 30 is rotatably coupled to the cap 36 which is attached to the cylinder 20.

Figure 7:
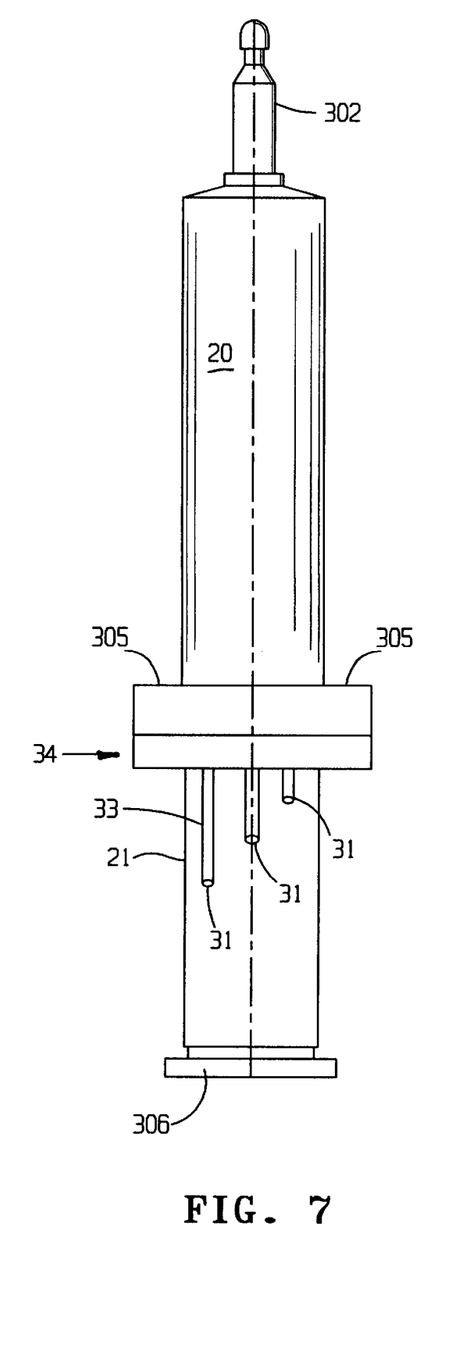
FIG. 7 is a side view of another embodiment of a syringe incorporating the dispensing mechanism of the present invention.
Figure 8:
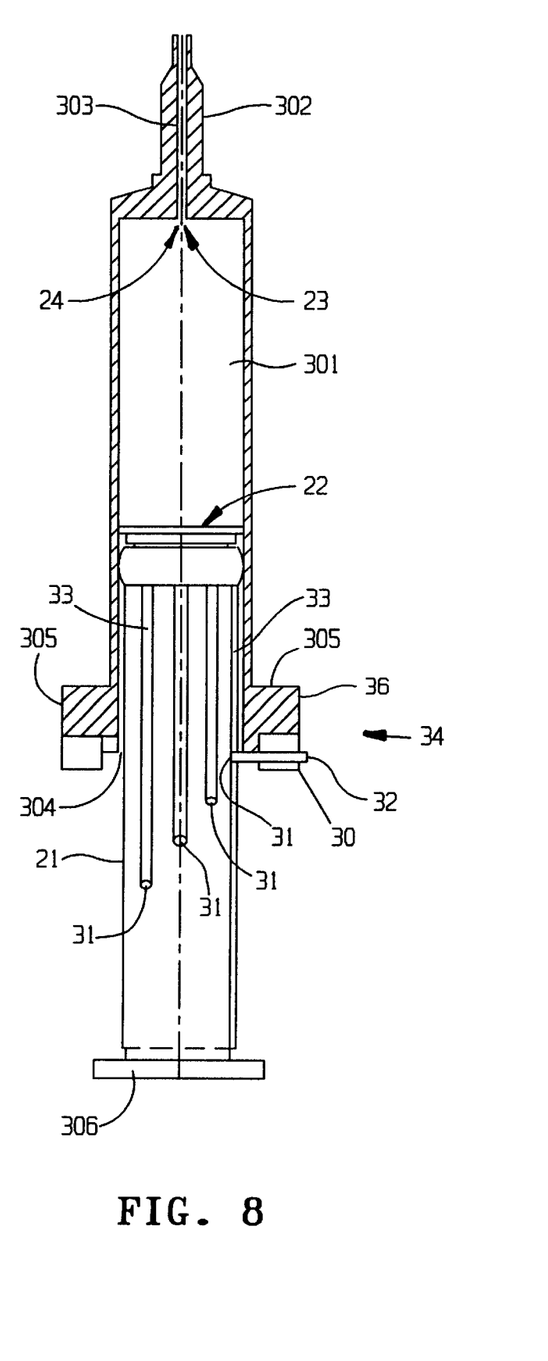
FIG. 8 is a side view, partially in cross section, of the syringe of FIG. 7.

FIGS. 7–8 illustrate another embodiment of a syringe applicator incorporating the dispensing mechanism of the present invention. In this embodiment, the circumferencial groove 35 intersects each of the longitudinal grooves 33 corresponding to the place on the plunger 21 proximate to the projection 32 when the plunger 21 has undergone a completed expansion stroke. The projection 32 extends inwardly from the stop member 36 and limits the compression stroke of the plunger, depending on the particular groove 33 in which the projection has entered. Thus, this embodiment can be used to meter desired volumes of material from pre-filled syringes. The grooves 33 would have staggered lengths, each groove 33 corresponding to an incremental increase in the volume dispensed. In operation, the projection 32 is initially aligned with the shortest groove 33 and the plunger 21 is pushed into the chamber 301 to distribute the first desired volume interval. The plunger 21 is then retracted back to its original position where the projection 32 is aligned with the circumferencial groove 35. The plunger 21 is then rotated so that a longer groove 33 is aligned with the projection 32. The plunger 21 is then pushed into the chamber 301 a little further than the first time, which distributes a second desired volume interval. This process can be repeated until the syringe is empty.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A dispensing mechanism for an applicator having a cylinder and a plunger, wherein the plunger has a piston head slidable in liquid-tight manner within the cylinder, and wherein the plunger performs an expansion stroke to draw fluid into the cylinder and performs a compression stroke to dispense fluid from the cylinder, said dispensing mechanism comprising:
    (a) a stop member attached to the cylinder of the applicator, said stop member having an engagement part; and
    (b) at least one abutment formed on the plunger for contacting said engagement part and for limiting motion of the plunger; and
wherein said stop member has an annular shape, wherein the plunger extends through said stop member, wherein said engagement part projection extending radially inward from said stop member, and wherein said projection is retractable through said engagement part.

2. The dispensing mechanism of claim 1, wherein said stop member moves relative with respect to the plunger, and wherein said relative movement includes longitude movement and rotational movement.

3. The dispensing mechanism of claim 2, wherein the plunger is non-rotatable with respect to the cylinder, and wherein said stop member is rotatable with respect to the cylinder.

4. The dispensing mechanism of claim 1, wherein the plunger has a cylindrically-shaped surface, wherein said at least one abutment comprises a plurality of circumferencially spaced abutments around the surface of the plunger.

5. The dispensing mechanism of claim 4, wherein said plurality of circumferencially spaced abutments are staggered along the length of the plunger, and wherein each of said plurality of circumferencially spaced abutments corresponds to a predetermined range of longitudinal movement by the plunger.

6. A dispensing mechanism for an applicator having a cylinder and a plunger, wherein the plunger has a piston head slidable in liquid-tight manner within the cylinder, and wherein the plunger performs an expansion stroke to draw fluid into the cylinder and performs a compression stroke to dispense fluid from the cylinder, said dispensing mechanism comprising:
    (a) a stop member attached to the cylinder of the applicator, said stop member having an engagement part; and
    (b) at least one abutment formed on the plunger for contacting said engagement part and for limiting motion of the plunger; and wherein each of said at least one abutment comprises an end wall of a longitudinal groove formed on a surface of the plunger.

7. The dispensing mechanism of claim 6, wherein said engagement part fits and tracks within said at least one longitudinal groove during both the expansion motion and the compression motion of the plunger.

8. The dispensing mechanism of claim 7, wherein the plunger is further formed with a circumferencial groove intersecting said at least one longitudinal groove, whereby relative rotational motion between said stop member and the plunger is effected when the engagement part is within said circumferencial groove.

9. The dispensing mechanism of claim 8, wherein said circumferencial groove intersects said at least one longitudinal groove at a point along the length of the plunger so that said engagement part enters said circumferencial groove when the plunger is fully compressed.

10. The dispensing mechanism of claim 1, further including a scale for indicating a dose volume corresponding to each of said at least one abutments.

11. A dispensing mechanism for dispensing measured doses of fluid from an applicator having a cylinder and a plunger, wherein the plunger has a piston head slidable in liquid-tight manner within the cylinder, and wherein the plunger performs an expansion stroke to draw fluid into the cylinder and performs a compression stroke to dispense fluid from the cylinder, said dispensing mechanism comprising:
    (a) a stop member attached to the cylinder of the applicator, said stop member having an annular shape to permit the plunger to extend through said stop member, said stop member further having an inwardly extending projection, wherein said stop member moves relative with respect to the plunger, and wherein said relative motion includes longitudinal motion; and
    (b) a plurality of circumferencially spaced longitudinal grooves formed in a surface of the plunger, each having a first end surface and a second end surface, wherein said first end surface forms an abutment for engaging with said projection and for limiting the expansion motion of the plunger, and wherein said projection fits and tracks within said plurality of longitude grooves during the expansion stroke and the compression stroke of the plunger.

12. A dispensing mechanism for dispensing measured doses of fluid from an applicator having a cylinder and a plunger, wherein the plunger has a piston head slidable in liquid-tight manner within the cylinder, and wherein the plunger performs an expansion stroke to draw fluid into the cylinder and performs a compression stroke to dispense fluid from the cylinder, said dispensing mechanism comprising:

(a) a stop member attached to the cylinder of the applicator, said stop member having an annular shape to permit the plunger to extend through said stop member, said stop member further having an inwardly extending projection, wherein said stop member moves relative with respect to the plunger, and wherein said relative motion include longitudinal motion and rotational motion; and (b) a plurality of circumferencially spaced longitudinal grooves formed in a surface of the plunger, each having a first end surface and a second end surface, wherein said first end surface forms an abutment for engaging with said projection and for limiting the expansion motion of the plunger, wherein said projection fits and tracks within said plurality of longitude grooves during the expansion stroke and the compression stroke of the plunger, wherein a circumferencial groove intersects said longitudinal grooves at said second end surface, and wherein said circumferencial groove is positioned along the plunger at a point where the projection enters the circumferencial groove when the plunger has been fully compressed.

13. An applicator for dispensing volumes of fluid, comprising:

(a) a cylinder;

(b) a plunger having a piston head slidable in liquid-tight manner within said cylinder, wherein said plunger performs an expansion stroke to draw fluid into said cylinder and performs a compression stroke to dispense fluid from said cylinder, and wherein said plunger is formed with at least one abutment; and (c) a stop member attached to said cylinder, wherein said stop member has an engagement part for contacting said at least one abutment and for limiting motion of the plunger; and wherein each of said at least one abuttment formed on said plunger comprises an end surface of a longitudinal groove formed in a surface of said plunger, wherein said engagement part is a projection extending from said stop member into a desired longitudinal groove, and wherein said projection tracks within said desired longitudinal groove during the expansion stroke and the compression stroke of said plunger.

14. The applicator of claim 13, wherein said plunger is further formed with a circumferencial groove intersecting each of said at least one longitudinal groove, and wherein said projection tracks within said circumferencial groove to allow relative rotational motion between said stop member and said plunger.

15. The applicator of claim 14, wherein said circumferencial groove is positioned on said plunger to allow said projection to track within said circumferencial groove to effect relative rotational motion between said stop member and said plunger on completion of a compression stroke by said plunger.

16. The applicator of claim 15, wherein said applicator is a syringe having a first end and an open second end, wherein said first end has a bore for drawing and expelling fluid, and wherein said piston head is received within and said plunger extends through said open second end.

17. The applicator of claim 15, further comprising an annular cap encircling said plunger, wherein said cap has a annular ledge, wherein said stop member rotates on said ledge, wherein said stop member is rotatable with respect to the cylinder, and wherein said plunger is not rotatable with respect to the cylinder.

18. The applicator of claim 15, further comprising a fluid ingress channel for drawing fluid into said cylinder during an expansion stroke, an intake one-way valve for preventing fluid from returning from said cylinder into said fluid ingress channel during a compression stroke, a fluid egress channel for expelling fluid from said cylinder during a compression stroke, an outtake one-way valve for preventing fluid from returning from said fluid egress channel into said cylinder during an expansion stroke.

19. The applicator of claim 15, further comprising a spring encircling said plunger, wherein said spring biases said plunger toward an expansion stroke.

20. The applicator of claim 19, wherein said applicator is a trigger pump comprising a body containing said cylinder and said plunger, a connection member attached to said body, and a trigger member attached to said plunger, wherein said connection member contains a portion of said fluid ingress channel and provides fluid communication means with a fluid source, wherein said plunger and said trigger member each contain a portion of said fluid egress channel, and wherein said trigger member provides a means to perform a compression stroke of said plunger.

21. The applicator of claim 19, wherein said applicator is an instrument comprising a fixed handle part attached to said cylinder, a movable handle part coupled to said plunger, wherein said fixed handle part and said movable handle part are pivotally connected, wherein squeezing said movable handle against said fixed handle performs a compression stroke of said plunger, wherein said plunger contains a portion of said fluid ingress channel, and wherein a connection member contains a portion of said fluid ingress channel and provides fluid communication means with a fluid source.

22. An applicator for dispensing measured volumes of fluid, comprising:

(a) a cylinder;

(b) a plunger having a piston head slidable in liquid-tight manner within said cylinder, wherein said plunger performs an expansion stroke to draw fluid into said cylinder and performs a compression stroke to dispense fluid from said cylinder;

(c) a stop member attached to the cylinder of the applicator, said stop member having an annular shape to permit the plunger to extend through said stop member, said stop member further having an inwardly extending projection, wherein said stop member has relative motion with respect to the plunger, and wherein said relative motion includes longitudinal motion and rotational motion; and (d) wherein said plunger is formed with a plurality of longitudinal grooves and a circumferencial groove, each of said longitudinal grooves having a first end surface and a second end surface, wherein said first end surface forms an abutment for engaging with said projection and for limiting the expansion motion of the plunger, wherein said projection fits and tracks within said plurality of longitude grooves during the expansion stroke and the compression stroke of the plunger, wherein said projection enters said circumferencial groove upon a completed compression stroke of said plunger.

23. A method for selecting and dispensing a volume of fluid from an applicator comprising a cylinder of predetermined fixed dimensions and a plunger, wherein the plunger has a piston head sealingly fit within the cylinder, wherein the plunger expels fluid from the cylinder during a compression stroke and draws fluid into the cylinder during an expansion stroke, and wherein the plunger has a plurality of longitudinal grooves of different lengths formed in its surface, the applicator further comprising a stop member having a projection sized to fit and track within the longitudinal grooves, said method comprising the steps of:

(a) expelling fluid from the cylinder by completing a compression stroke of the plunger, wherein the projection tracks within a first longitudinal groove during the compression stroke;

(b) selecting a desired second longitudinal groove to limit the expansion stroke of the plunger to draw in the desired dose of fluid into the cylinder;

(c) moving the projection from the first longitudinal groove into the second longitudinal groove;

(d) drawing the desired volume of fluid into the cylinder through an expansion stroke of the plunger until the projection which is tracking in the second longitudinal groove contacts an end surface of the second longitudinal groove; and (e) expelling the desired volume from the cylinder by completing a compression stroke, wherein the projection tracks within the second longitudinal groove.

24. The method for selecting and dispensing a volume of fluid from an applicator of claim 23, wherein the plunger has a circumferencial groove formed in its surface, wherein the circumferencial groove intersects the longitudinal groove, and wherein said step of moving the projection from the first longitudinal groove into the second longitudinal groove includes the steps of tracking the projection from the first longitudinal groove into the circumferencial groove by completing the compression stroke, and rotating the stop member until the projection which is tracking in the circumferencial groove is aligned with the second longitudinal groove.

* * * * *